United States Patent
Colin

(10) Patent No.: US 7,238,638 B2
(45) Date of Patent: *Jul. 3, 2007

(54) COMPOSITE COPPER/TIN/ALKALI METAL CATALYSTS FOR THE DIRECT SYNTHESIS OF ALKYLHALOSILANES

(75) Inventor: Pascale Colin, Chassieu (FR)

(73) Assignee: Rhodia Chimie, Aubervilliers (FR)

( * ) Notice: Subject to any disclaimer, the term of this patent is extended or adjusted under 35 U.S.C. 154(b) by 0 days.

This patent is subject to a terminal disclaimer.

(21) Appl. No.: 11/148,323

(22) Filed: Jun. 9, 2005

(65) Prior Publication Data

US 2005/0283017 A1    Dec. 22, 2005

Related U.S. Application Data

(63) Continuation of application No. PCT/FR03/03613, filed on Dec. 8, 2003.

(51) Int. Cl.
*B01J 27/00* (2006.01)
*B01J 23/02* (2006.01)
*B01J 23/70* (2006.01)
*C07F 7/00* (2006.01)
*C07F 7/04* (2006.01)

(52) U.S. Cl. .............. 502/208; 502/344; 502/345; 502/352; 556/472; 556/473; 556/477

(58) Field of Classification Search ........... 502/208, 502/344, 345, 352; 556/472, 473, 477
See application file for complete search history.

(56) References Cited

U.S. PATENT DOCUMENTS

| 4,656,301 | A | * | 4/1987 | Prud'Homme et al. | ..... 556/472 |
| 4,661,613 | A | * | 4/1987 | Prud'Homme et al. | ..... 556/472 |
| 4,762,940 | A | * | 8/1988 | Halm et al. | ................ 556/472 |
| 4,962,220 | A | * | 10/1990 | Halm et al. | ................ 556/473 |
| 4,966,986 | A | * | 10/1990 | Halm et al. | ................ 556/473 |
| 5,312,948 | A | * | 5/1994 | Freeburne et al. | .......... 556/472 |
| 5,596,119 | A | * | 1/1997 | Halm et al. | ................ 556/472 |

* cited by examiner

*Primary Examiner*—J. A. Lorengo
*Assistant Examiner*—Patricia L. Hailey
(74) *Attorney, Agent, or Firm*—Buchanan, Ingersoll & Rooney, PC

(57) ABSTRACT

The alkylhalosilanes are directly synthesized while diminishing the formation of coke by reacting an alkyl halide with silicon in the presence of a catalytically effective amount of (α) a copper metal or a copper-based compound catalyst and (β) a catalyst promoter intermixture therefor which comprises an effective minor amount of an additive β1 selected from the group consisting of tin, a tin-based compound and mixture thereof, optionally, an effective minor amount of an additive β2 selected from the group consisting of zinc metal, a zinc-based compound and mixture thereof, an effective minor amount of an additive β3 selected from the group consisting of cesium, potassium and rubidium, and compound and mixture thereof, and, optionally, an effective minor amount of an additive β4 selected from the group consisting of the element phosphorus, a phosphorus-based compound and mixture thereof.

42 Claims, No Drawings

COMPOSITE COPPER/TIN/ALKALI METAL CATALYSTS FOR THE DIRECT SYNTHESIS OF ALKYLHALOSILANES

CROSS-REFERENCE TO PRIORITY/PCT APPLICATIONS

This application claims priority under 35 U.S.C. § 119 of FR 02/15532, filed Dec. 9, 2002, and is a continuation of PCT/FR 2003/003613, filed Dec. 8, 2003 and designating the United States (published in the French language on Jul. 29, 2004 as WO 2004/063206 A1; the title and abstract were also published in English), each hereby expressly incorporated by reference and each assigned to the assignee hereof.

CROSS-REFERENCE TO COMPANION APPLICATION

Copending application Ser. No. 11/148,204, filed concurrently herewith and also assigned to the assignee hereof.

BACKGROUND OF THE INVENTION

1. Technical Field of the Invention

The present invention relates to novel material compositions comprising copper, tin, an alkali metal and, optionally, zinc and/or phosphorus as catalytic systems especially suited for the direct synthesis of alkylhalosilanes by contacting an alkyl halide with silicon and which makes it possible to conduct this direct synthesis while substantially reducing the formation of coke.

2. Description of Background and/or Related and/or Prior Art

The industrial process for the manufacture of alkylhalosilanes and, for example, of dimethyldichlorosilane, subsequently referred to as DMDCS, is a well known process which is described in particular in U.S. Pat. No. 2,380,995 and in the text by Walter Noll, *Chemistry and Technology of Silicones*, 1968, published by Academic Press Inc., London, pages 26–41.

According to this "direct synthesis" or "Rochow synthesis" process, the alkylhalosilanes, for example DMDCS, are manufactured directly by reaction of methyl chloride with a solid contact body formed of silicon and of a catalyst comprising copper, according to the reaction:

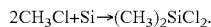

$$2CH_3Cl + Si \rightarrow (CH_3)_2SiCl_2.$$

In reality, other coproducts, such as in particular those indicated below, are formed during the direct synthesis: other alkylhalosilanes, such as methyltrichlorosilane $CH_3SiCl_3$, subsequently referred to as MTCS, and trimethylchlorosilane $(CH_3)_3SiCl$, subsequently referred to as TMCS; halogenated alkylhydrosilanes, such as, for example, methylhydrodichlorosilane $(CH_3)HSiCl_2$, subsequently referred to as MHDCS; and heavy products which are polysilanes and in particular disilanes, such as, for example, trimethyltrichlorodisilane $(CH_3)_3Si_2Cl_3$ and dimethyltetrachlorodisilane $(CH_3)_2Si_2Cl_4$.

Among all the products obtained by direct synthesis, the dialkyldihalosilane, and for example DMDCS, is the main product, that is to say the product obtained in predominant amount. This product is highly desirable as, after hydrolysis and polymerization, it makes it possible to obtain oils and gums which are base products for the manufacture of silicones.

It is known to use copper, whether in the form of copper metal or in the form of copper-based chemical compounds, as catalyst of the direct synthesis reaction.

In order, in particular:
  to improve the mean activity (also referred to as productivity) of the contact body comprising the combination based on silicon and on catalyst, this activity (or productivity) being evaluated as weight of the silanes obtained per hour and per kilogram of silicon initially involved,
  to also improve the selectivity for the dialkyldihalosilane, and for example for DMDCS, evaluated, for example, by the mol % of DMDCS with respect to all the silanes obtained and by the MTCS/DMDCS mean ratio by weight, and
  to lower the content by weight of "heavy" products with respect to the silanes obtained, it has to date been proposed to add, to the copper, a promoter combination comprising one or more promoting additive(s). These additives can be: zinc or a zinc halide (U.S. Pat. No. 2,464,033), aluminum (U.S. Pat. Nos. 2,403,370 and 2,427,605), tin, manganese, nickel and silver (GB-A-1-207,466), cobalt (GB-A-907,161), potassium chloride (SU-A-307,650), or arsenic or an arsenic compound (U.S. Pat. No. 4,762,940).

EP-A-0-138,678 and EP-A-0-138,679 describe the use of a copper catalyst as a mixture with an improved promoter combination which includes:
  30 to 1,000 ppm (calculated as weight of metal with respect to the weight of silicon involved) of at least one metal selected from among tin and antimony or of a compound based on tin and/or on antimony,
  optionally 0.1 to 3% (calculated as indicated above) of zinc metal or of a zinc-based compound, and
  in the case of EP-A-0-1 38,678: 0.05 to 4% (calculated as indicated above) of cesium or of a cesium compound, taken alone or as a mixture with at least one other alkali metal selected from among lithium, sodium, potassium, rubidium and a compound based on said alkali metal; or, in the case of EP-A-0-138,679: 0.05 to 2% (calculated as indicated above) of at least one alkali metal selected from among lithium, sodium, potassium, rubidium and a compound based on said same alkali metal.

U.S. Pat. No. 4,601,101 describes the use of a copper catalyst as a mixture with another improved promoter combination which includes:
  5 to 200 ppm (calculated as weight of metal with respect to the weight of silicon involved) of tin or of a tin-based compound,
  optionally 100 to 10,000 ppm (calculated as indicated above) of zinc metal or of a zinc-based compound, and
  25 to 931 ppm (calculated as indicated above) of elemental phosphorus, of a metal phosphide and/or of a compound capable of providing a metal phosphide in the reaction body of the direct synthesis.

However, despite the importance of the catalytic systems (copper catalyst as a mixture with a promoter combination) provided in the abovementioned prior art, research continues in this field as the industrial conditions for implementation of the direct synthesis process give rise, in a manner known per se [cf. *Journal of Catalysis*, 161, 861–866 (1996)], to side reactions in which the starting alkyl halide is cracked, which side reactions result in the formation of coke and of hydrocarbons. This formation of coke is the cause in particular of the fouling of the direct synthesis reactor(s) within which coke is deposited. This undesirable fouling requires that periodic cleaning operations be carried out, which accordingly reduces the productive capacity of the plant.

SUMMARY OF THE INVENTION

It has now surprisingly been found that the use of appropriate catalytic systems comprising a promoter combination in which additives based on tin and an alkali metal and optionally on zinc and/or phosphorus are present makes it possible to carry out the direct synthesis while decreasing the undesirable formation of coke.

According to the present invention, a catalytic system is employed appropriate for the implementation of the process for the preparation of alkylhalosilanes by reaction of an alkyl halide, preferably $CH_3Cl$, with a solid body, referred to as contact body, formed of silicon and of a catalytic system comprising (α) copper metal or a copper-based compound and (β) a promoter combination.

More specifically, the present invention features catalytic systems comprising (α) copper metal or a copper-based compound and (β) a promoter combination comprising:

10 to 500 ppm (calculated as weight of metal with respect to the weight of silicon involved) of an additive β1 selected from among tin, a tin-based compound and a mixture of these entities, optionally 0.01 to 3% (calculated as weight of metal with respect to the weight of silicon involved) of an additive β2 selected from among zinc metal, a zinc-based compound and a mixture of these entities, 0.01 to 2% (calculated as weight of metal with respect to the weight of silicon involved) of an additive β3 selected from among cesium, potassium and rubidium, a compound based on said alkali metal and a mixture of these entities, and optionally 50 to 3,000 ppm (calculated as weight of elemental phosphorus with respect to the weight of silicon involved) of an additive β4 selected from among the element phosphorus, a phosphorus-based compound and a mixture of these entities.

DETAILED DESCRIPTION OF BEST MODE AND SPECIFIC/PREFERRED EMBODIMENTS OF THE INVENTION

In the present invention, the indicator which was selected in order to quantitatively assess the undesirable formation of coke is, in the case, for example, where the starting alkyl halide is $CH_3Cl$, the % by weight of MHDCS with respect to the totality of the silanes obtained in the direct synthesis. The cracking of the starting alkyl halide takes place, in the case, for example, of methyl chloride, according to the following reaction (not balanced):

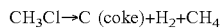

and it is known that the more cracking there is, the greater the amount of MHDCS, which is directly related to the production of hydrogen.

The catalyst (α) can be used at a content by weight ranging from 1 to 20%, preferably ranging from 2 to 12%, with respect to the weight of silicon involved.

Use may be made, in place of copper metal, of a copper compound, in particular of: a copper halide, such as, for example, cuprous chloride or cupric chloride; a copper carboxylate, such as, for example, cuprous formate, cupric formate, cuprous acetate or cupric acetate; or a copper oxide, such as, for example, $Cu_2O$ or $CuO$.

It has been demonstrated, in accordance with the present invention, that better results, in particular for selectivity and for degree of conversion of the silicon, are obtained if the copper is introduced in the form of copper metal and/or in the form of cuprous chloride.

The content by weight of tin and/or of tin compound (compulsory promoting additive β1, the content of which is calculated as weight of tin metal) advantageously ranges from 10 to 500 ppm and preferably from 30 to 300 ppm, with respect to the weight of silicon involved.

It is necessary to have at least 10 ppm of tin metal. This is because it has been found in accordance with the invention that the beneficial effects of the promoting additives β3 based on an alkali metal and/or on a compound of an alkali metal and optionally β4 based on phosphorus are only obtained in the presence of tin and/or of a tin compound. In addition, a content by weight of greater than 500 ppm would have a harmful effect on the reaction and in particular on the selectivity.

Use is made, as tin-based compound, for example, of tin chloride. The promoting additive β1 which is preferably used is tin metal; advantageously, this tin metal can be added in the form of bronze.

According to the embodiment defined above, the catalytic system optionally comprises a promoting additive β2 based on zinc metal and/or on a zinc compound; when such a promoting additive is used, it is preferably zinc metal and/or zinc chloride.

The zinc, when it is used, is present at a content by weight ranging from 0.01 to 3%, preferably from 0.02 to 0.5% (calculated as zinc metal with respect to the weight of silicon involved).

The content by weight of alkali metal and/or of alkali metal compound (compulsory promoting additive 3, the content of which is calculated as alkali metal) advantageously ranges from 0.01 to 2% by weight and preferably from 0.05 to 1.0% by weight. Below 0.01% by weight, the action of the alkali metal is not really detectable and, above 2% by weight, the alkali metal does not have the expected effect on the selectivity.

Use may be made, as compound of an alkali metal selected from among Cs, K and Rb, of: halides, and for example the chloride; or carboxylates, and for example the formate or the acetate. Cesium chloride, potassium chloride, rubidium chloride and/or a mixture of these compounds are the promoting additives β3 which are preferably used.

According to the embodiment defined above, the catalytic system optionally comprises a further promoting additive β4 based on phosphorus and/or on a phosphorus compound. When such a promoting additive is used, and this is a preferential step for the implementation of the invention in the case where the reaction is carried out without resorting to an additive β2 based on zinc and/or on a zinc compound, the content by weight of elemental phosphorus and/or of compound based on phosphorus (promoting additive β4, the content of which is calculated as weight of elemental phosphorus) ranges from 50 to 3,000 ppm and preferably from 80 to 1,500 ppm and more preferably still from 90 to 800 ppm. Below 50 ppm, the action of the phosphorus is not really detectable and, above 3,000 ppm, the phosphorus has a poisonous effect which reduces the selectivity.

The phosphorus which is used in the present invention as promoting additive can be elemental phosphorus, such as, for example, red phosphorus, white phosphorus and black phosphorus. Use may be made, as phosphorus-based compound, of: metal phosphides, and for example aluminum phosphide, calcium phosphide $Ca_3P_2$, copper phosphide $Cu_3P$, nickel phosphide $NiP_2$, tin phosphide SnP, the iron phosphides FeP, $Fe_2P$ and $Fe_3P$, the zinc phosphides $Zn_3P_2$ and $ZnP_2$, or silicon phosphide; or phosphorus-based compounds capable of forming metal phosphides of the type of those mentioned above during the direct synthesis reaction between the alkyl halide and the contact body based on silicon and on the catalytic system $(\alpha)+(\beta)$. Use may also be made, as other phosphorus-based compounds, of certain alloys which are known to comprise both phosphorus and a metal part and which are readily available commercially, for example the copper-phosphorus alloys which comprise approximately from 7 to 15% by weight of phosphorus. Copper phosphide $Cu_3P$ and the copper-phosphorus alloys are the promoting additives $\beta4$, when the choice is made to use one of them, which are the preferred.

When a promoting additive $\beta4$ is used, it is arranged for, more preferably, the amounts of the additives $\beta3$ and $\beta4$ to be selected within the abovementioned regions of general and preferred variation so that the ratio:

$$\frac{\text{number of gram atoms of alkali metal}}{\text{number of gram atoms of elemental phosphorus}}$$

varies from 1 to 20, preferably from 1.2 to 15 and more preferably still from 1.5 to 12.

Also, it is desirable for the particle size of the silicon to be such that the mean diameter of at least 50% by weight of the particles ranges from 10 to 500 μm and preferably from 60 to 200 μm. Likewise, the catalyst $(\alpha)$ and the group of promoters $(\beta)$ are also advantageously in the form of particles, the mean diameter of at least 50% by weight of the particles advantageously ranging from 1 to 100 μm.

The direct synthesis process according to the invention can generally be carried out in one of the three following types of apparatus: a reactor of the stirred bed type, such as that described in U.S. Pat. No. 2,449,821, a reactor of the fluidized bed type, such as that described in U.S. Pat. No. 2,389,931, or a rotary kiln.

The constituent ingredients of the catalytic system $(\alpha)+(\beta)$ can also be used deposited on a particulate inorganic material, such as sand, ground silica, silica gel, alumina, ground refractory brick, catalysts for the cracking of oil, zeolites and calcined clays, as described in FR-A-1,545,407.

The direct synthesis reaction advantageously is carried out at a temperature ranging from 280 to 400° C. and preferably from 300 to 380° C. It can be carried out, in total or in part, under an absolute pressure of alkyl halide equal to atmospheric pressure (1 bar) or greater than atmospheric pressure; when the latter case prevails, the reaction is generally carried out under an absolute pressure ranging from 1.1 to 8 bar and preferably ranging from 1.5 to 4 bar.

In order to carry out the direct synthesis reaction, an initial stage of activation of the contact body (formed by the combination based on silicon+catalyst+promoters) is advantageously performed beforehand, as is well known; one of the activation means which is highly suitable can entail heating said contact body to a certain temperature which can be, by a few degrees to several tens of degrees, less than or greater than the temperature selected for the direct synthesis reaction and which is within the general or preferred range mentioned above.

On using the catalytic system $(\alpha)+(\beta)$ according to the invention, it is possible to obtain, for example, when the reaction is carried out, both in a stirred bed and in a fluidized bed, at a temperature ranging from 280° C. to 400° C. and preferably ranging from 300 to 380° C., a % by weight of MHDCS, with respect to all the silanes obtained in the direct synthesis (indicator which was selected for quantitatively assessing the undesirable formation of coke), which can be as low as 0.15% by weight; this % by weight of MHDCS is generally less than 0.60% by weight.

The values obtained with regard to % by weight of MHDCS, with respect to all the silanes obtained in the direct synthesis, in the proportions such as those mentioned above, appear as particularly surprising with regard to the teachings of the prior art, which have remained completely silent to date on the nature of the catalytic systems which make it possible to carry out the direct synthesis while decreasing the undesirable formation of coke.

As regards the mean activity of the catalytic system, it is, for example, on the order of or greater than 300 g of silanes/h/kg of Si, being able to reach 335 g of silanes/h/kg of Si and more.

As regards the selectivity, evaluated, for example, by the mean mol % of DMDCS with respect to all the silanes obtained and by the MTCS/DMDCS mean ratio by weight:
  mean mol % of DMDCS: the value obtained is on the order of or greater than 90%, being able to reach 93% and more,
  MTCS/DMDCS mean ratio by weight: the value obtained is on the order of or less than 0.05, being able to reach 0.035 and even less.

As regards the percentage of heavy products formed with respect to the silanes obtained, it can be as low as 1.5% by weight and it is generally less than 3% by weight.

In order to further illustrate the present invention and the advantages thereof, the following specific examples are given, it being understood that same are intended only as illustrative and in nowise limitative. In said examples to follow, all parts and percentages are given by weight, unless otherwise indicated.

In the following examples, unless otherwise mentioned, use is made of a cylindrical pilot-scale reactor with an internal diameter of 60 mm and a height of 250 mm equipped at its base with a sparger made of sintered glass. The silicon and the catalytic system are charged in the form of a powder, the mean size of at least 50% by weight of the particles of which ranges from 60 to 200 μm. The reaction is carried out in a stirred bed and the reactor is equipped with an external heating element.

EXAMPLES

Example 1

Catalytic System: Cu/Sn/Cs:

A powder of 210 g of silicon, 16.4 g of CuCl, 0.38 g of bronze comprising 10% by weight of tin, and 1.9 g of CsCl is charged to a cylindrical vertical glass reactor equipped with a metal stirrer and with a sparger made of sintered glass.

The reactor is gradually heated to 200° C. under a stream of nitrogen. Then, while continuing to raise the temperature of the reactor, the nitrogen tap is closed and the introduction is begun of the methyl chloride with a flow rate, measured at 20° C., of 60 g/h.

The temperature of the reactor is regulated at 360° C. and the methyl chloride flow rate is maintained at 60 g/h for 8 hours; the test takes place at atmospheric pressure.

This test produced silanes with a mean productivity or activity of 302 g of silanes per hour and per kg of Si initially charged to the reactor.

The mixture produced is analyzed by gas chromatography and it is characterized by:
- a % by weight of MHDCS of 0.25%,
- a mean mol % of DMDCS of 92.4%.

The MTCS/DMDCS ratio obtained is equal to 0.040 (% by weight/% by weight).

The proportion of "heavy" products (polysilanes) obtained amounts to 2.3% by weight.

Example 2

Catalytic System: Cu/Zn/Sn/Cs:

A powder of 210 g of silicon, 16.4 g of CuCl, 1.64 g of $ZnCl_2$, 0.38 g of bronze comprising 10% by weight of tin, and 1.9 g of CsCl is charged to a cylindrical vertical glass reactor equipped with a metal stirrer and with a sparger made of sintered glass.

The reactor is gradually heated to 200° C. under a stream of nitrogen. Then, while continuing to raise the temperature of the reactor, the nitrogen tap is closed and the introduction is begun of the methyl chloride with a flow rate, measured at 20° C., of 60 g/h.

The temperature of the reactor is regulated at 360° C. and the methyl chloride flow rate is maintained at 60 g/h for 8 hours; the test takes place at atmospheric pressure.

This test produced silanes with a mean productivity or activity of 234 g of silanes per hour and per kg of Si initially charged to the reactor.

The mixture produced is analyzed by gas chromatography and it is characterized by:
- a % by weight of MHDCS of 0.50%,
- a mean mol % of DMDCS of 92.9%.

The MTCS/DMDCS ratio obtained is equal to 0.039 (% by weight/% by weight).

The proportion of "heavy" products (polysilanes) obtained amounts to 1.5% by weight.

Example 3

Catalytic System: Cu/Sn/Cs/P (1029 ppm):

A powder of 210 g of silicon, 16.4 g of CuCl, 0.38 g of bronze comprising 10% by weight of tin, and 1.9 g of CsCl is charged to a cylindrical vertical glass reactor equipped with a metal stirrer and with a sparger made of sintered glass. After initiating the reaction and when the performance has stabilized (i.e., after reacting for 4 hours), 3 g of $Cu_3P$ comprising 7.2% by weight of phosphorus are added.

The reactor is gradually heated to 200° C. under a stream of nitrogen. Then, while continuing to raise the temperature of the reactor, the nitrogen tap is closed and the introduction is begun of methyl chloride with a flow rate, measured at 20° C., of 60 g/h.

The temperature of the reactor is regulated at 360° C. and the methyl chloride flow rate is maintained at 60 g/h. The reaction is halted by the operator after maintaining at 360° C. for 4 hours in order to allow the addition of $Cu_3P$ when the reactor has reached ambient temperature. Once the addition has been carried out, the rise in temperature and the introduction of $CH_3Cl$ are controlled as above.

The test takes place at atmospheric pressure. The test is halted by the operator after producing methylchlorosilanes (MCSs) for 8 hours.

This test produced silanes with a mean productivity or activity of 335 g of silanes per hour and per kg of Si initially charged to the reactor.

The mixture produced is analyzed by gas chromatography and it is characterized by:
- a % by weight of MHDCS of 0.15%,
- a mean mol % of DMDCS of 93.3%.

The MTCS/DMDCS ratio obtained is equal to 0.037 (% by weight/% by weight).

The proportion of "heavy" products (polysilanes) obtained amounts to 1.7% by weight.

Example 4

Catalytic System: Cu/Zn/Sn/Cs/P (1029 ppm):

A powder of 210 g of silicon, 16.4 g of CuCl, 1.64 g of $ZnCl_2$, 0.38 g of bronze comprising 10% by weight of tin, and 1.9 g of CsCl is charged to a cylindrical vertical glass reactor equipped with a metal stirrer and with a sparger made of sintered glass. After initiating the reaction and when the performance has stabilized (i.e., after reacting for 4 hours), 3 g of $Cu_3P$ comprising 7.2% by weight of phosphorus are added.

The reactor is gradually heated to 200° C. under a stream of nitrogen. Then, while continuing to raise the temperature of the reactor, the nitrogen tap is closed and the introduction is begun of methyl chloride with a flow rate, measured at 20° C., of 60 g/h.

The temperature of the reactor is regulated at 360° C. and the methyl chloride flow rate is maintained at 60 g/h. The reaction is halted by the operator after maintaining at 360° C. for 4 hours in order to allow the addition of $Cu_3P$ when the reactor has reached ambient temperature. Once the addition has been carried out, the rise in temperature and the introduction of $CH_3Cl$ are controlled as above.

The test takes place at atmospheric pressure. The test is halted by the operator after producing methylchlorosilanes (MCSs) for 8 hours.

This test produced silanes with a mean productivity or activity of 235 g of silanes per hour and per kg of Si initially charged to the reactor.

The mixture produced is analyzed by gas chromatography and it is characterized by:
- a % by weight of MHDCS of 0.45%,
- a mean mol % of DMDCS of 92.6%.

The MTCS/DMDCS ratio obtained is equal to 0.042 (% by weight/% by weight).

The proportion of "heavy" products (polysilanes) obtained amounts to 1.5% by weight.

Comparative Test:

Catalytic System: Cu/Zn/Sn:

A powder of 210 g of silicon, 16.4 g of CuCl, 1.64 g of $ZnCl_2$ and 0.38 g of bronze comprising 10% by weight of tin is charged to a cylindrical vertical glass reactor equipped with a metal stirrer and with a sparger made of sintered glass.

The reactor is gradually heated to 200° C. under a stream of nitrogen. Then, while continuing to raise the temperature of the reactor, the nitrogen tap is closed and the introduction is begun of the methyl chloride with a flow rate, measured at 20° C., of 60 g/h.

The temperature of the reactor is regulated at 360° C. and the methyl chloride flow rate is maintained at 60 g/h for 8 hours; the test takes place at atmospheric pressure.

This test produced silanes with a mean productivity or activity of 326 g of silanes per hour and per kg of Si initially charged to the reactor.

The mixture produced is analyzed by gas chromatography and it is characterized by:

a % by weight of MHDCS of 0.76%,
a mean mol % of DMDCS of 86.8%.

The MTCS/DMDCS ratio obtained is equal to 0.074 (% by weight/% by weight).

The proportion of "heavy" products (polysilanes) obtained amounts to 3.7% by weight.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the direct synthesis of alkylhalosilanes while diminishing the undesirable formation of coke, comprising reacting an alkyl halide with silicon in the presence of a catalytically effective amount of ($\alpha$) a copper metal or a copper-based compound catalyst and ($\beta$) a catalyst promoter intermixture therefor which comprises an effective minor amount of an additive $\beta 1$ selected from the group consisting of tin, a tin-based compound and mixture thereof, optionally, an effective minor amount of an additive $\beta 2$ selected from the group consisting of zinc metal, a zinc-based compound and mixture thereof, an effective minor amount of an additive $\beta 3$ selected from the group consisting of cesium, potassium and rubidium, and compound and mixture thereof, and, an effective minor amount of an additive $\beta 4$ selected from the group consisting of the element phosphorus, a phosphorus-based compound and mixture thereof; wherein the additives $\beta 3$ and $\beta 4$ are present in such amounts that the ratio:

$$\frac{\text{number of gram atoms of alkali metal}}{\text{number of gram atoms of elemental phosphorus}}$$

ranges from 1 to 20.

2. The process as defined by claim 1, said catalyst promoter intermixture comprising from 10 to 500 ppm of additive $\beta 1$, optionally, from 0.01% to 3% of additive $\beta 2$, from 0.01% to 2% of additive $\beta 3$ and, from 50 to 3,000 ppm of additive $\beta 4$, each by weight with respect to the weight of the silicon.

3. The process as defined by claim 2, comprising up to 3% of additive $\beta 2$.

4. The process as defined by claim 3, said catalyst promoter intermixture comprising from 0.02% to 0.5% of additive $\beta 2$.

5. The process as defined by claim 3, said additive $\beta 2$ comprising zinc metal and/or zinc chloride.

6. The process as defined by claim 2, comprising up to 3,000 ppm of additive $\beta 4$.

7. The process as defined by claim 6, said catalyst promoter intermixture comprising from 80 to 1,500 ppm of additive $\beta 4$.

8. The process as defined by claim 6, said additive $\beta 4$ comprising copper phosphide $Cu_3P$ and/or a copper-phosphorus alloy.

9. The process as defined by claim 2, comprising up to 3% of additive $\beta 2$ and up to 3,000 ppm of additive $\beta 4$.

10. The process as defined by claim 2, said catalyst promoter intermixture comprising from 30 to 300 ppm of additive $\beta 1$.

11. The process as defined by claim 2, said catalyst promoter intermixture comprising from 0.05% to 1.0% of additive $\beta 3$.

12. The process as defined by claim 1, said additive $\beta 1$ comprising tin metal.

13. The process as defined by claim 12, said additive $\beta 1$ comprising bronze.

14. The process as defined by claim 1, said additive $\beta 3$ comprising cesium chloride, potassium chloride, rubidium chloride, and/or mixture thereof.

15. The process as defined by claim 1, said ratio ranging from 1.2 to 15.

16. The process as defined by claim 1, said ratio ranging from 1.5 to 12.

17. The process as defined by claim 1, comprising from 1% to 20% by weight of said catalyst ($\alpha$), with respect to the weight of the silicon.

18. The process as defined by claim 1, said catalyst ($\alpha$) comprising copper metal, cuprous chloride and/or mixture thereof.

19. The process as defined by claim 1, carried out at a temperature ranging from 280° C. to 400° C.

20. The process as defined by claim 1, the silicon comprising particulates thereof, the mean diameter of at least 50% by weight of said particles ranging from 10 to 500 µm.

21. The process as defined by claim 20, the catalyst ($\alpha$) and catalyst promoter intermixture ($\beta$) also comprising particulates thereof, the mean diameter of at least 50% by weight of said particles ranging from 1 to 100 µm.

22. The process as defined by claim 21, said particulate catalyst ($\alpha$) and catalyst promoter intermixture ($\beta$) being deposited onto a particulate inorganic support therefor.

23. The process as defined by claim 1, the mean mol % of DMDCS produced relative to the total amount of silanes produced being at least 90%.

24. The process as defined by claim 1, the mean ratio by weight of MTCS/DMDCS produced being no greater than 0.05.

25. The process as defined by claim 1, said alkyl halide comprising methyl chloride.

26. A composite catalyst system suited for catalyzing the direct synthesis of alkylhalosilanes while diminishing the undesirable formation of coke, comprising a catalytically effective amount of ($\alpha$) a copper metal or a copper-based compound catalyst and ($\beta$) a catalyst promoter intermixture therefor which comprises an effective minor amount of an additive $\beta 1$ selected from the group consisting of tin, a tin-based compound and mixture thereof, optionally, an effective minor amount of an additive $\beta 2$ selected from the group consisting of zinc metal, a zinc-based compound and mixture thereof, an effective minor amount of an additive $\beta 3$ selected from the group consisting of cesium, potassium and rubidium, and compound and mixture thereof, and, an effective minor amount of an additive $\beta 4$ selected from the group consisting of the element phosphorus, a phosphorus-based compound and mixture thereof; wherein the additives $\beta 3$ and $\beta 4$ are present in such amounts that the ratio:

$$\frac{\text{number of gram atoms of alkali metal}}{\text{number of gram atoms of elemental phosphorus}}$$

ranges from 1 to 20.

27. The composite catalyst system as defined by claim 26, said catalyst promoter intermixture comprising from 10 to 500 ppm of additive $\beta1$, optionally, from 0.01% to 3% of additive $\beta2$, from 0.01% to 2% of additive $\beta3$ and, from 50 to 3,000 ppm of additive $\beta4$, each by weight with respect to the weight of the silicon.

28. The composite catalyst system as defined by claim 27, comprising up to 3% of additive $\beta2$.

29. The composite catalyst system as defined by claim 28, said catalyst promoter intermixture comprising from 0.02% to 0.5% of additive $\beta2$.

30. The composite catalyst system as defined by claim 28, said additive $\beta2$ comprising zinc metal and/or zinc chloride.

31. The composite catalyst system as defined by claim 27, comprising up to 3,000 ppm of additive $\beta4$.

32. The composite catalyst system as defined by claim 31, said catalyst promoter intermixture comprising from 80 to 1,500 ppm of additive $\beta4$.

33. The composite catalyst system as defined by claim 31, said additive $\beta4$ comprising copper phosphide $Cu_3P$ and/or a copper-phosphorus alloy.

34. The composite catalyst system as defined by claim 27, comprising up to 3% of additive $\beta2$ and up to 3,000 ppm of additive $\beta4$.

35. The composite catalyst system as defined by claim 27, said catalyst promoter intermixture comprising from 30 to 300 ppm of additive $\beta1$.

36. The composite catalyst system as defined by claim 27, said catalyst promoter intermixture comprising from 0.05% to 1.0% of additive $\beta3$.

37. The composite catalyst system as defined by claim 26, said additive $\beta1$ comprising tin metal.

38. The composite catalyst system as defined by claim 37, said additive $\beta1$ comprising bronze.

39. The composite catalyst system as defined by claim 26, said additive $\beta3$ comprising cesium chloride, potassium chloride, rubidium chloride, and/or mixture thereof.

40. The composite catalyst system as defined by claim 26, said catalyst ($\alpha$) comprising copper metal, cuprous chloride and/or mixture thereof.

41. The composite catalyst system as defined by claim 26, the catalyst ($\alpha$) and catalyst promoter intermixture ($\beta$) comprising particulates thereof, the mean diameter of at least 50% by weight of said particles ranging from 1 to 100 µm.

42. The composite catalyst system as defined by claim 41, said particulate catalyst ($\alpha$) and catalyst promoter intermixture ($\beta$) being deposited onto a particulate inorganic support therefor.

* * * * *